United States Patent [19]
Pliura et al.

[11] Patent Number: 5,545,328
[45] Date of Patent: * Aug. 13, 1996

[54] PURIFICATION OF HEMOGLOBIN BY DISPLACEMENT CHROMATOGRAPHY

[75] Inventors: Diana H. Pliura, Mississauga; Diane E. Wiffen, Georgetown, both of Canada; Salman Ashraf, Raleigh, N.C.; Anthony A. Magnin, Willowdale, Canada

[73] Assignee: Hemosol Inc., Etobicoke, Canada

[*] Notice: The portion of the term of this patent subsequent to Aug. 8, 2012, has been disclaimed.

[21] Appl. No.: 406,148

[22] Filed: Mar. 20, 1995

Related U.S. Application Data

[63] Continuation-in-part of Ser. No. 308,538, Sep. 21, 1994, which is a continuation-in-part of Ser. No. 187,316, Jan. 27, 1994, Pat. No. 5,439,591.

[30] Foreign Application Priority Data

Sep. 21, 1993 [CA] Canada ................................. 2106612

[51] Int. Cl.$^6$ ................................................. B01D 15/08
[52] U.S. Cl. ................. 210/635; 210/656; 210/198.2; 530/385; 530/413; 530/416; 530/417
[58] Field of Search ......................... 210/635, 656, 210/659, 198.2; 530/385, 413, 416, 417

[56] References Cited

U.S. PATENT DOCUMENTS

| | | | |
|---|---|---|---|
| 3,971,842 | 7/1976 | Ewbank | 210/656 |
| 4,599,175 | 7/1986 | Yamamizu et al. | 210/635 |
| 4,764,279 | 8/1988 | Tayot | 210/656 |
| 4,925,575 | 5/1990 | Hsia | 210/635 |
| 5,028,696 | 7/1991 | Torres et al. | 210/656 |
| 5,043,423 | 8/1991 | Viscomi et al. | 530/344 |
| 5,084,558 | 1/1992 | Rausch et al. | 530/385 |
| 5,149,436 | 9/1992 | Taniguchi | 210/656 |
| 5,250,665 | 10/1993 | Kluger et al. | 530/385 |
| 5,264,555 | 11/1993 | Shorr et al. | 530/385 |
| 5,340,474 | 8/1994 | Kauvar | 210/198.2 |
| 5,439,591 | 8/1995 | Pliura | 210/635 |

OTHER PUBLICATIONS

Christensen, "Preparation of Human Hemoglobin Ao for Possible Use as a Blood Substitute", J. Biochem. Phys. 17 (1988) pp. 143–154.

Winslow & Chapman "Pilot–Scale Preparation of Hemoglobin Solutions", Methods in Enzymology, vol. 231, p. 3 (1994).

*Primary Examiner*—Ernest G. therkorn
*Attorney, Agent, or Firm*—Ridout & Maybee

[57] ABSTRACT

A preselected hemoglobin species is separated from contaminants having a different acidity from that of the preselected hemoglobin species, by an overload displacement chromatography process. To remove more acidic contaminants, the process is conducted under anion exchange conditions. To remove more basic contaminants, the process is conducted under cation exchange conditions. In either case, the exchange column is overloaded to displace the hemoglobin species therefrom with contaminants having greater affinity for the column, and using the impure hemoglobin solution as the displacer.

12 Claims, 6 Drawing Sheets

PURIFICATION OF HEMOGLOBIN BY DISPLACEMENT CHROMATOGRAPHY

CROSS REFERENCE TO RELATED APPLICATIONS

This application is a continuation-in-part of U.S. patent application Ser. No. 08/308,538 filed Sep. 21, 1994, which is in turn a continuation-in-part of U.S. patent application Ser. No. 08/187,316 filed Jan. 27, 1994, now U.S. Pat. No. 5,439,591.

FIELD OF THE INVENTION

This invention relates to protein purification, and more particularly to chromatographic processes for purifying hemoglobin.

BACKGROUND OF THE INVENTION AND PRIOR ART

The development of hemoglobin based blood substitutes continues to command commercial attention, and recent developments have shown that hemoglobin from mammalian blood cells, after suitable modification such as intramolecular crosslinking and in some instances polymerization, shows great promise as the basis of a blood substitute. As development has proceeded, however, the requirements for purity of the hemoglobin have steadily increased. At one time it was believed that hemoglobin simply needed to be stroma free, a condition achieved by washing and gentle lysing of the red blood cells, followed by filtration of the lysate. Subsequently, it was found that the presence of trace residues of impurities such as phospholipids led to more specific reactions, e.g. vasoconstriction, to the product in animal trials. Even after the product has been subjected to several diafiltration steps, it still contains unacceptably high traces of potentially harmful impurities such as erythrocyte enzymes, modified and variant forms of hemoglobin, phospholipids and surface antigens.

A hemoglobin-based blood substitute needs to be based either on a single hemoglobin species, or, if more than one species is present, a carefully controlled composition of known hemoglobin species. Accordingly, a successful hemoglobin purification process needs to be capable of separating one hemoglobin form from another, as well as separating the desired hemoglobin form from contaminating red blood cell such components such as erythrocyte enzymes, proteins, phospholipids and antigens.

Chemical crosslinking of hemoglobin for the preparation of the basis of a blood substitute commonly produces a mixture of hemoglobin species. These should subsequently be separated. Since they are in many cases of almost identical molecular weight and chemical composition, their separation presents difficulties.

Art example of a crosslinking reagent which produces a mixture of hemoglobin species, some crosslinked between certain pairs of positions on globin chains and others between other such positions, along with modified, uncrosslinked material and unchanged starting material, is the trig acyl (methyl phosphate) ester of 1,3,5-benzenetricarboxylic acid (TMMP), as disclosed in U.S. Pat. No. 5,250,665 Kluger et. al., issued Oct. 5, 1993.

Chromatographic methods have been applied to the purification of hemoglobin solutions. U.S. Pat. No. 4,925,474 Hsia et. al. describes the application of the techniques of affinity chromatography to hemoglobin purification, using columns in which a ligand showing preferential chemical binding affinity to the DPG site of hemoglobin was bound to the stationary phase of the column.

Ion exchange chromatographic techniques have also been applied to hemoglobin purification. The basic principles of the techniques of ion exchange chromatography are well known. A mixture of different species in a solution is applied to a suitably prepared ion exchange column. Each of the species in the mixture has a different affinity for the chemical reactant groups on the column. By varying the conditions on the column, e.g. the pH of the solution, the individual species can be arranged to bind or to elute from the column selectively, so as to separate one species individually from the mixture. The application of the technique to the purification of proteins such as hemoglobin is economically unattractive, except when used for small scale operations and analytical work. When hemoglobin is to be purified on a manufacturing scale, for use for example as an oxygen carrying resuscitative fluid (blood substitute), the technique, as conventionally applied, is impractical. The amounts of hemoglobin to be absorbed on and subsequently eluted from a chromatography column are so large that the column size requirements become impractically large and expensive.

Christensen et al., J. Biochem. Phys. 17 (1988), 143–154, reported the chromatographic purification of human hemoglobin. The methodology used represented a standard ion exchange chromatographic approach that did not provide opportunities for economical scale-up to production levels.

Winslow and Chapman, "Pilot-Scale Preparation of Hemoglobin Solutions," *Methods in Enzymology,"* Vol. 231 p3 (1994) describe the preparation of stroma free hemoglobin (SFH), highly purified hemoglobin A0 and crosslinked hemoglobin using outdated human blood as starting material. The SFH is prepared by filtration, The Hemoglobin A0 is prepared from SFH by process scale chromatography using a strong anion-exchange medium and an ionic strength gradient.

U.S. Pat. No. 5,084,588 Rausch and Feola (Biopure), describes standard anion and cation exchange chromatography methods for application to separation and purification of hemoglobin. In the case of anion exchange chromatography, three standard approaches are listed in this patent:

a) binding of the Hb at elevated pH, and elution with a descending pH gradient or step gradient of lower pH;

b) binding of the Hb at high pH, low ionic strength and elution with a salt gradient;

c) loading under pH conditions where the hemoglobin does not bind to the anion exchanger, but passes through the column unretained, while the impurities (more acidic contaminants) are captured on the column.

Approaches a) and b) have been extensively documented, but are not attractive for large scale production, owing to the limitation of low loading capacities necessary to achieve sufficient resolution of the hemoglobin products. These loading capacities are routinely only 20–30 mg/ml, and dictate prohibitively large and expensive columns for commercial scale purification of hemoglobin. For example, a single 50 gm dose of final hemoglobin-based oxygen carrier (HBOC) would require a column of 1.5–2.5 liters.

Whilst approach c) would appear on the surface to be the most practicable, it turns out in practice that the chromatographic properties of normal human adult, unmodified hemoglobin Ao and some of the major contaminants, such as HbAlc, are not sufficiently distinct for practical application of this approach.

The standard approaches to cat ion exchange chromatography of mammalian hemoglobin have similar limitations.

U.S. Pat. No. 5,084,588 also discloses bovine hemoglobin solutions in which more than 99.9% of the protein present is bovine hemoglobins, but does not present identifying data for the protein constituents.

SUMMARY OF THE INVENTION

It is an object of the present invention to provide a novel chromatographic process for the separation of contaminants from a selected hemoglobin species.

The present invention provides a process whereby an aqueous solution of at least one preselected hemoglobin species, Hb, in which the Hb constitutes from about 50% to about 99% of the dissolved material, is subjected to ion exchange chromatography in a self-displacement, overload manner. When it is desired to remove contaminants which are more acidic than the selected hemoglobin species, anion exchange chromatography is used. When it is desired to remove contaminants which are more basic than the selected hemoglobin species, cation exchange chromatography is used. In either case, a crude solution of the preselected hemoglobin species, e.g. HbA0 or a mixture of different hemoglobin species including the preselected species, is fed to the chromatographic column under conditions chosen so that all the constituents of the mixed solute are initially adsorbed on the solid phase of the chromatographic column. For anion exchange, for example, this requires a relatively high pH. The conditions are also chosen so that very high effective loading of the column is achieved, using low ionic strength of feed solution, leading to a situation in which substantially all of the accessible sites on the solid chromatographic medium are occupied by species of the feed solution. The initial eluant collected at this stage is devoid of protein product. Displacement of the preselected hemoglobin species and the contaminants having lower affinity for the column under the chosen conditions is then achieved by loading additional volumes of aqueous feed solution as defined above. The condition thereby achieved, herein referred to as an overload condition, causes contaminant species having greater affinity for the column to displace the selected Hb and the contaminant species having lesser affinity for the column, to be eluted from the column. When this is anion exchange chromatography, contaminants which are more acidic than the selected Hb species are adsorbed on the solid phase of the chromatographic column, and are thereby separated from the selected Hb species, which appears in the eluate along with the more basic contaminants. In the case where cation exchange chromatography is selected, the more basic contaminants are separated, by greater affinity to the column, with the more acidic contaminants and the selected hemoglobin species appearing in the eluate.

Contaminants more acidic than the selected Hb species, or more basic than the selected Hb species, depending upon the selection, remain attached to the column resin. The column can be easily regenerated using traditional cleaning and regeneration procedures.

An important factor in the successful operation of the process is the selective, high loading of the column with either the basic impurities or the acidic impurities, allowing the Hb species to elute. High loadings are particularly advantageous if the process is to be scaled up to commercial size.

BRIEF REFERENCE TO THE DRAWINGS

DESCRIPTION OF THE PREFERRED EMBODIMENTS

Figure 1:
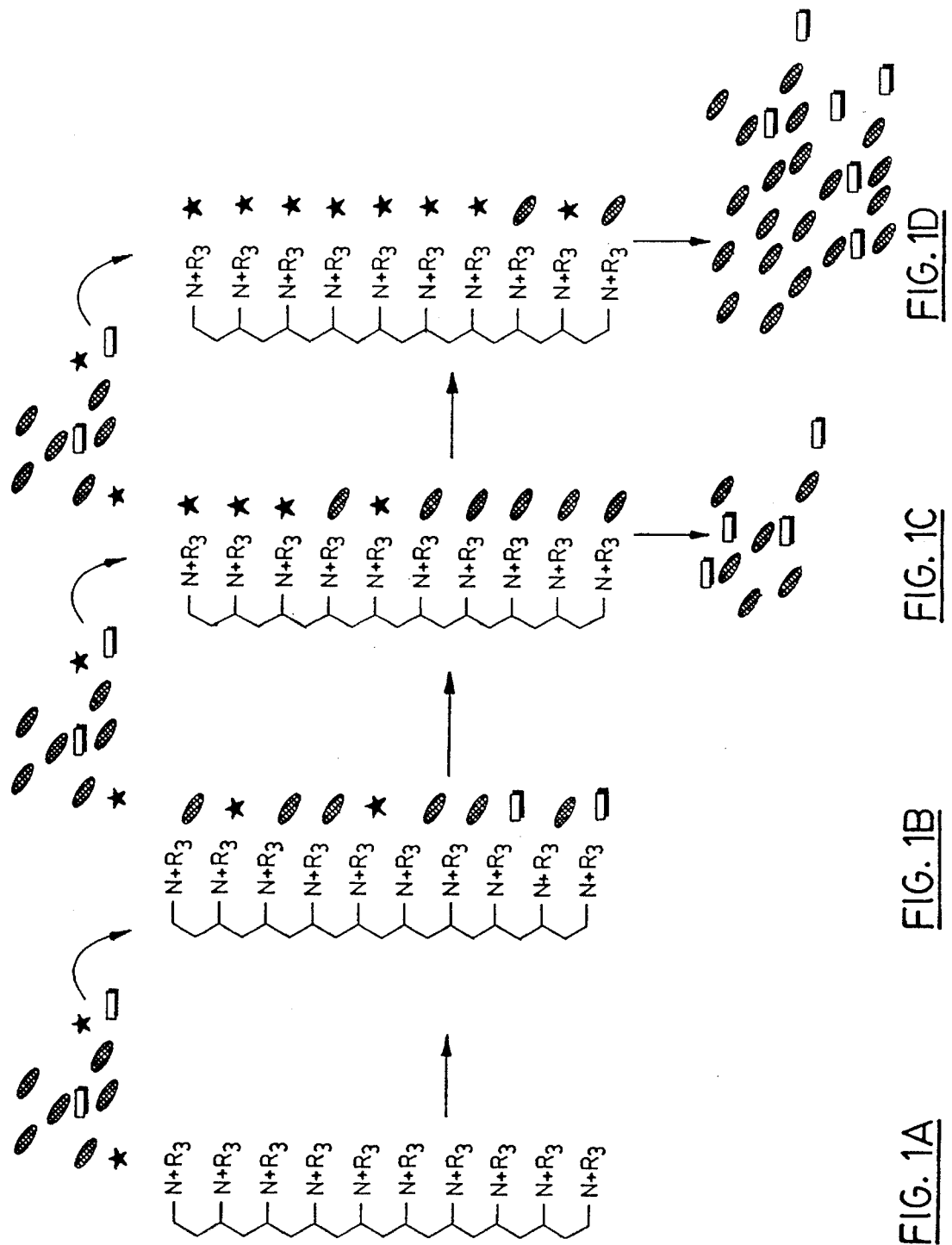
FIGS. 1A through 1D are a diagrammatic illustration of the principles of the process of the present invention, as applied to anionic exchange.

Displacement chromatography, or displacement elution as it is commonly termed, is a known technique in the field of protein separation. It is one of the three modes by which a sample is recovered from a chromatography column. As applied to separation of respective proteins from a mixture of proteins in solution, proteins of greater affinity will displace proteins of lesser affinity on the matrix, so that a hierarchy of proteins in descending order of affinity is set up within the column, from inlet to outlet. When proteins displace other proteins, a sharp line of demarcation between the species is rarely formed. The application of the technique to prepare highly pure solutions of a single protein such as a hemoglobin is thus contraindicated. If a separate, non-proteinaceous displacing species is chosen, the result may be that the chromatography matrix has bound to it materials having a very high affinity, which is very difficult to regenerate for re-use.

The process is useful in preparation of purified adult human hemoglobin Ao (HbAo), for removing the more acidic contaminants therefrom or for removing the more basic contaminants therefrom. The process can also be applied to similar purification of other preselected hemoglobin species such as selected crosslinked hemoglobin derivatives, selected bovine hemoglobin variants, other hemoglobin variants, such as fetal hemoglobin species, sickle cell hemoglobin species etc., genetically engineered hemoglobin species, etc. It is particularly beneficial for use in circumstances where all or substantially all of the contaminants of the selected hemoglobin species are more acidic than the selected hemoglobin species, or more basic than the selected hemoglobin species. In these cases purified hemoglobin species can be obtained in a single chromatographic step.

A specific example of where this occurs, and therefore constituting a particularly preferred embodiment of the invention, is in the purification of the product resulting from the chemical crosslinking of hemoglobin with TMMP, mentioned above. The hemoglobin species resulting from this process which is most desirable for forming the basis of a hemoglobin-based oxygen carrier (HBOC), is a combination of two species having substantially identical physiological properties, namely one which is three-point crosslinked between $\beta$ globin chains, specifically at positions $82\beta'$-$82\beta$-$1\beta$, and one which is two-point crosslinked $82\beta'$-$1\beta$. These are processes and products described in the aforementioned U.S. Pat. No. 5,250,665 Kluger et. al., where this three-point crosslinked material is designated $\beta^1{}_{82}$>X-82$\beta$ and the two-point crosslinked material is designated $\beta1$-X-82$\beta$. This combination TM-Hb commonly constitutes only 50–60% of all the hemoglobin species in the reaction mixture. When the non-crosslinked hemoglobin products and unreacted starting materials have been separated therefrom, by routine chemical means, the remaining hemoglobin contaminants are all more acidic than the preselected species. Accordingly, the process of the present invention, utilizing anionic exchange chromatography, is particularly suitable and preferred for use with such mixed hemoglobin products.

The process of the invention is extremely attractive economically, for use on a commercial scale, e.g. in the production of blood substitutes. It provides very high effective column loading capacities. It can consequently utilize relatively small size columns, to purify relatively large volumes of impure hemoglobin solution. Moreover, the impure hemoglobin solution itself is used as the displacement medium. The provision and use of a separate displacer, with its attendant inconveniences, complications and expense, is thereby avoided.

A typical overall process for making a purified HbAo solution involving the technique of the present invention starts with normal adult, human red blood cells. These are pooled and optionally subjected to filtration to remove leukocytes. The cells are washed to remove serum proteins and lysed to extract the hemoglobin and other cell components. The lysate is filtered to remove red cell membrane and then the resultant hemoglobin solution is diafiltered and concentrated. The impure hemoglobin extract is treated with carbon monoxide to form a CO-Hb complex and heated to pasteurize it, thereby inactivating vital contaminants in the solution. It is then centrifuged and filtered, to remove further remnants and cellular debris. It is now ready to be subjected to the self-displacement process of the present invention.

According to one preferred embodiment of the invention, the chromatographic process is the anion exchange process, thereby removing the more acid contaminants from the mixture containing the selected hemoglobin species. This anion exchange process is preferably run at high pH, e.g. pH 7–10 and preferably pH 8.5–9.0, and under conditions of low ionic strength i.e. low conductivity. The conductivity is suitably less than 3 mS (milli Siemens) and preferably less than 1 mS. Such conditions involve an essentially salt free buffer. The desired hemoglobin species will initially bind to the column medium under these conditions, along with all other species. As the feed of impure hemoglobin solution to the column continues, those species which show greater affinity than the hemoglobin for the matrix, namely the more acidic contaminants, gradually displace the hemoglobin species and more basic contaminants from the column. Eventually, an overload of the column is achieved, so that the hemoglobin species and more basic contaminants are displaced, leaving the more acidic contaminants bound thereto. In most cases, this is a loading far in excess of the column manufacturer's recommendations. The chromatographic separation of the more acidic contaminants from hemoglobin species is thus achieved.

The feed of the impure hemoglobin solution is conducted at a slow linear flow rate, not greater than 10 cm per minute, and preferably at about I cm per minute. This permits kinetic equilibration of the column. The feed concentration range is not critical, but is suitably in the range 0.1–20%, preferably 2–7%.

The achievement of the overload condition can be monitored by analysis of the column effluent—when the composition of the effluent shows none, or only traces, of acidic impurity, the maximum practical loading of the column has been achieved.

FIG. 1 of the accompanying drawings diagrammatically illustrates the anionic exchange process of the present invention. The ion exchange column having chemical groups, $-N^+R_3$ (typical of anionic exchange resins, but exemplary only), shown at stage A Of the process in FIG. 1 is fed with a solution containing a mixture of species represented by stars, for the more acidic contaminants, ellipses representing selected hemoglobin species, and rectangles representing the more basic contaminants. At capacity loading, stage B, substantially all the active chemical groups N—$R_3$ of the column have bound by electrostatic charge to one of the species contained in the mixture.

More of the same solution is fed to the capacity loaded column to reach an overload condition, illustrated in stage C of FIG. 1. Now, all of the more basic contaminants (rectangles) and some of the hemoglobin (represented by ellipses) are displaced therefrom by the more acidic component (represented by stars), which exhibits the greater affinity for the column under these conditions. Feed of even more of the same solution to the overloaded column continues, to reach stage D illustrated on FIG. 1, at which the acidic species has displaced substantially all of the hemoglobin from the column, because of its greater affinity under the chosen conditions. Now the effluent issuing from the column contains substantially no detectable amounts of the acidic contaminants. A fairly pure solution of hemoglobin, but still containing some more basic species (contaminants), is thus obtained.

In the preferred embodiment of the invention, there are no basic contaminants in the starting mixture with the preselected species, i.e. no contaminants represented by rectangles. Then, pure preselected hemoglobin species elutes from the column eventually.

The alternative manner of practicing the preferred process of the present invention uses a cationic exchange column, and is fed with a mixture of the preselected hemoglobin species with contaminants which are more basic than selected hemoglobin species. This could, for example, be the eluant from anionic column which has been produced as described above. The mixture is supplied to the column to a similar overloaded condition. The desired hemoglobin species and other, unwanted, more basic, impurities are bound in overloaded amounts. The mixture continues to be fed to the cationic column. Relatively slow feed rates are again employed, suitably 10 cm/min or less, and preferably about 1 cm/min, to permit kinetic equilibration of the solid phase and the liquid phase. The pH of the eluant feed solution is suitably adjusted to the range pH 5–9, preferably pH 6.5–8.5, and most preferably pH 7–8, prior to loading of mixture onto the cation exchange column. Low ionic strength of the solution is used, i.e. conductivity less than 3 mS preferably less than 1 mS. Conductivities as large as 2.5 mS are only useful if very slow flow rates and very high feed dilutions are used. Again, overload conditions are used. The proteinaceous contaminants of higher affinity, i.e. those more basic than the hemoglobin species, displace the hemoglobin species from the column, and the hemoglobin species is thus eluted and recovered in exceptionally pure form.

Figure 2:
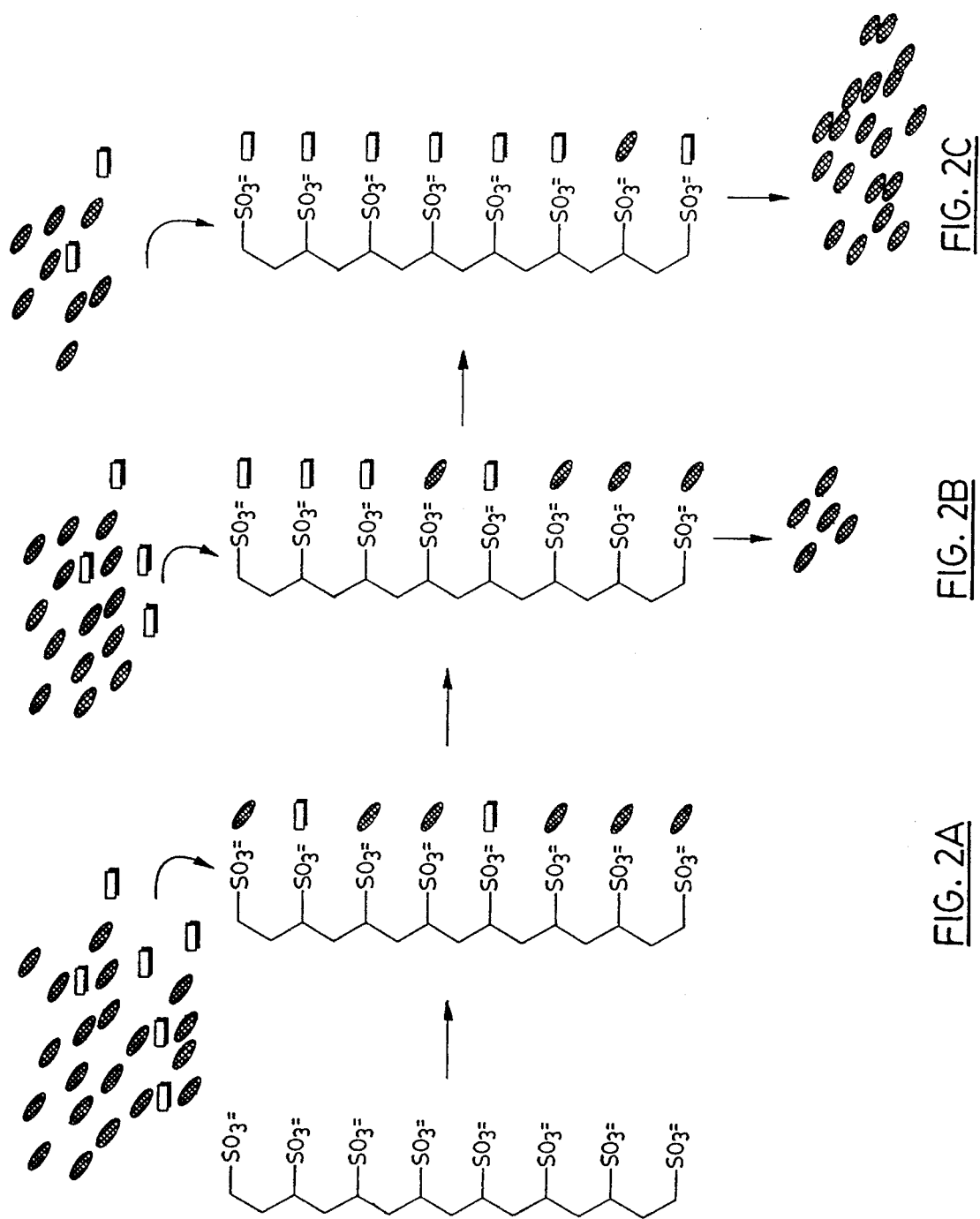
FIGS. 2A through 2C are a diagrammatic illustration, similar to FIGS. 1A–1D, of the principles of the process of the present invention, as applied to cationic exchange.

FIG. 2 of the accompanying drawings diagrammatically illustrates, in a manner similar to FIG. 1, the process taking place in the cation exchange column, shown carrying $SO_3$ groups. The mixture, after suitable pH adjustment, is fed to the column, and initially, in stage A, capacity loading is achieved with both the hemoglobin species (ellipses) and the more basic contaminants (rectangles) binding electrostatically to the chemical groups on the column. Whilst these are illustrated as sulfonic groups, other alternatives such as carboxyl groups could equally well be chosen. Feed of solution to the column continues to achieve an overload condition illustrated in stage B of FIG. 2, in which the more basic contaminant, on account of its greater affinity for the column under these conditions, is replacing the hemoglobin on the column. By continuing the feed to the overloaded column, as illustrated at stage C on FIG. 2, almost 100% pure hemoglobin species is thus displaced and obtained in solution as the eluent from the column. The higher the column loading accordingly, the higher the percentage recovery of purified hemoglobin species from the column. The eluant is monitored to detect the presence of basic species (rectangles) in the eluant. No further recovery of hemoglobin species by displacement from the column is achieved and maximum loading is defined at that point.

The more basic contaminants, as the term is used herein, refers to those contaminants which elute from the column at a higher pH than that required to elute the selected hemoglobin species. Conversely, the term "more acidic contaminants" refers to those contaminants which elute from the column at a lower pH than that required to elute the selected hemoglobin species.

Whether an anionic column or a cationic column is chosen in the present invention, the flow rates of the impure hemoglobin solution should be optimized for the selected concentration of the impure hemoglobin solution. Linear flow rates of 1 cm/min or less are optimal for hemoglobin solutions at the more concentrated range of 2–7%. Flow rates as high as 2 cm/min can be successfully applied to the resolution of more dilute solutions, for example less than 1% Hb. Resolution for ion exchange chromatography at low loading capacities is usually insensitive to linear flow rate; however, for the process of the present invention, kinetic equilibration during chromatography is highly dependent on flow rate. The concentration of the feed, however, is not critical in either stage.

The self-displacement chromatography process of the present invention can be run quickly, with reasonably small columns. It can be run under low pressure conditions and at ambient temperatures. Effective loading capacities which are 10–20 times the capacities reported for conventional chromatographic processes can be attained, making possible the use of relatively small column volumes. This leads to reductions in water requirements, reduced waste disposal and reduced buffer requirements, all of which improve significantly the commercial economics of the process.

The purified hemoglobin solution constituting the eluant from the exchange column can be diafiltered into a buffer of choice, and adjusted to the desired hemoglobin species concentration.

There is nothing particularly critical about the ion exchange gel material used in the process of the present invention as the stationery phase. The choice is well within the skill of the art. There can be used any of the common, commercially available such gels, provided that they can be successfully derivatized to operate in an ion exchange mode under the selected affinity conditions for the species to be separated. General classes of supports for ion exchange media include macroporous, macroreticular and non-porous types, divinylbenzene-crosslinked polystyrenes or polymethacrylates, polyalkyleneamines, cellulose, dextran, agarose, silica, ceramic, glass, alumina and metallic particles and others. Commercially available supports include those sold under the trade-marks POROS media, Fractogel, HyperD, Dowex, Amberlite, Duolite, Bio-Rex, Chelex, Sephadex, Sepharose, Toyopearl, Macro-prep, Bio-protocol, Accell, Mono types and others. Functional groups attached to such supports for the purpose of ion exchange include sulphonate, sulphopropyl, carboxymethyl, carboxylate, phospho, quaternaryamine, quaternary aminoethyl, polyethyleneimine, trimethylaminoethyl, diethylaminoethyl, aspartamide and others.

The invention is further described, for illustrative purposes, by the following, non-limiting examples.

SPECIFIC DESCRIPTION OF THE MOST PREFERRED EMBODIMENTS

Example 1—Preparation of Crude Hb Lysate

Ninety-six units (approx. 30 L) of packed red blood cells (RBCs) of the same blood type were pooled, and then diluted with 24 L of 0.9% saline solution. This pool was then filtered through 20µ and 8µ polypropylene filters to remove any residual leukocytes.

After leukocyte filtration, the RBCs were washed with 6 volumes of 0.9% saline in a constant volume diafiltration using $3.5m^2$ of 0.3µ Sepracor polyethersulphone hollow fibre membranes. The washing buffer was then replaced with 50 mM Tris lysing buffer, and the RBCs were gradually lysed into 6 volumes of this lysing buffer.

The crude lysate was collected and concentrated from approximately 2.5% Total Hemoglobin (THb) to approximately 9.0% THb busing a 30K Molecular Weight Cut Off (MWCO) Millipore PTTK membrane. Once concentrated, the tank was charged with CO gas to convert the hemoglobin to COHb form. The lysate was pasteurized at 62±2° C. for 10 hours in a jacketed tank. The pasteurized lysate was cooled and then centrifuged. Further depth filtration through Millipore 0.8µ filters prepared the pasteurized lysate for diafiltration on another Millipore 30K PTTK membrane. The material was diafiltered with 5 mM Tris, pH 8.9 until its conductivity was <0.3 mS and the pH was 8.9±0.2. It was then diluted to 4.5–5% THb, at which point it was ready for subsequent chromatographic purification.

Example 2—Self-Displacement Chromatography on Anion Exchange Resin

A 1×10 cm column packed with the anionic exchange resin PerSeptive Poros HQ-50 was washed with 4 column volumes of 1N NaCl and equilibrated with 5 mM Tris buffer, pH 8.8. After equilibration 50 ml of a 3.0% (3 g/100 ml) crude hemoglobin lysate (~85% HbAo) in 5 mM Tris, prepared as described in Example 1, pH 8.8, was loaded onto the column at 0.78 ml/min (1 cm/min). The column was overloaded to an effective capacity of 200 mg of the solute per ml of resin, and the eluant was collected. The column was then washed with 2 column volumes of 5 mM Tris, pH 8.8 buffer and this eluant was pooled with eluant collected during loading. The column was then washed with 1N NaCl to sluts the retained proteins, and this wash eluant was discarded. The hemoglobin eluant from the anion-exchange resin was analyzed on an analytical anion-exchange column using a pH gradient, as described in more detail below, in Example 8. It was determined to be about 95–96% HbAo, as shown on FIG. 3, with recovery of 90% of the HbAo loaded on to the column.

Example 3—Self Displacement Chromatography on Anion Exchange Resin

Figure 3:
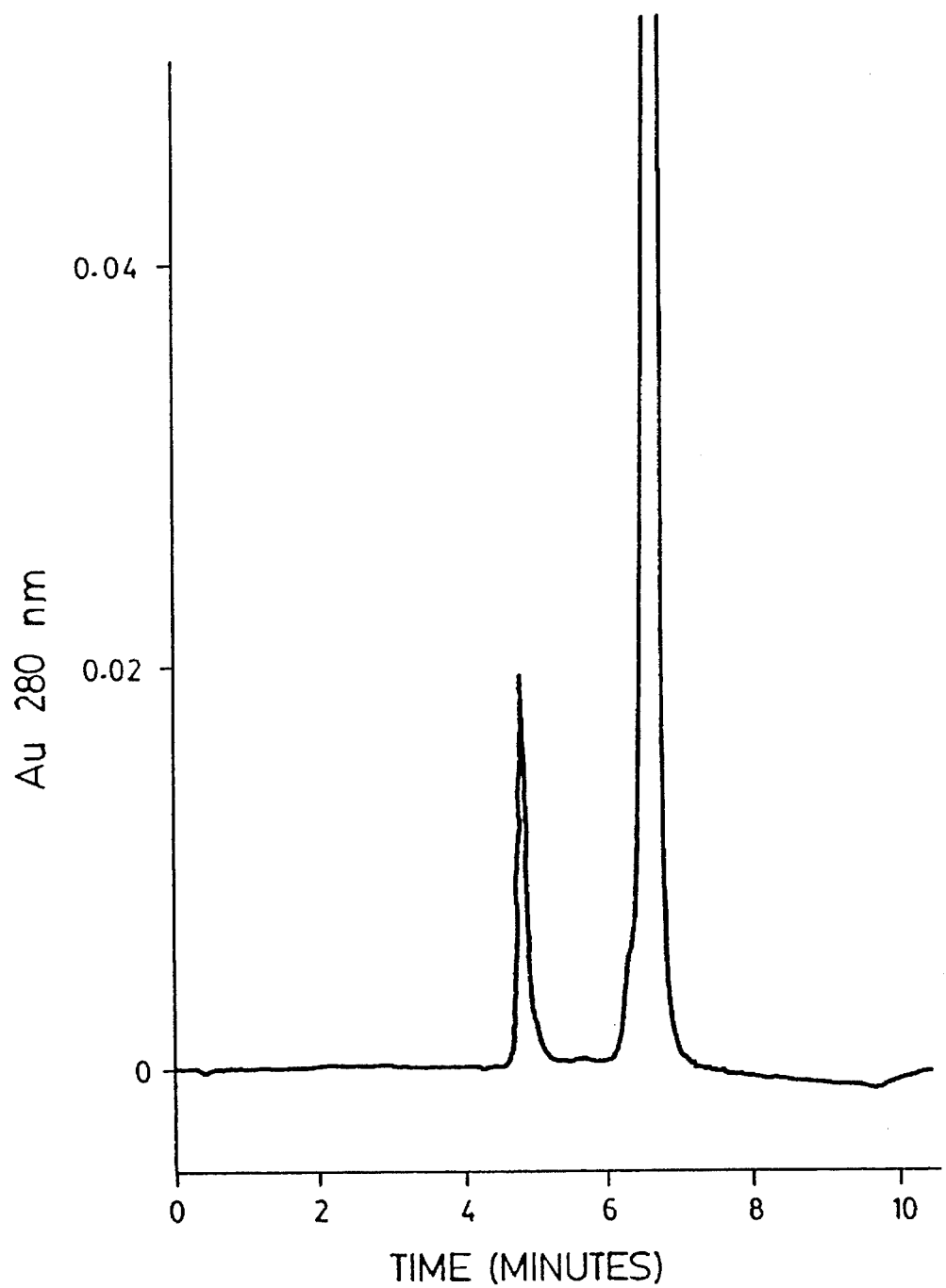
FIG. 3 is an analytical anion exchange chromatogram derived from the results of Examples 2 and 3 below.

A 1×10 cm column packed with Merck Fractogel-TMAE was washed with 4 column volumes of 1N NaCl and equilibrated with 5 mM Tris buffer, pH 8.8. After equilibration, 50 ml of a 3.0% (3 g/100 ml) crude hemoglobin lysate (~85% HbAo) in 5 mM Tris, prepared as described in Example 1, pH 8.8, was loaded onto the column at 0.78 mL/min (1 cm/min). This similarly led to an eventual overload of the column. The eluant was collected. The column was then washed with 2 column volumes of 5mM Tris, pH 8.8 buffer and this eluant was pooled with eluant collected during loading. The column was then washed with 1N NaCl to elute the retained proteins, and the wash eluant was discarded. The hemoglobin eluant from the anion-exchange resin was analyzed on an analytical anion-exchange column using a pH gradient, as described in more detail below in Example 8, determined to be about 95–96% HbAo, as shown in FIG. 3, with a recovery of 73% of the HbAo loaded on to the column.

Example 4—Self-Displacement Chromatography on a Cation-Exchange Resin

Figure 4:
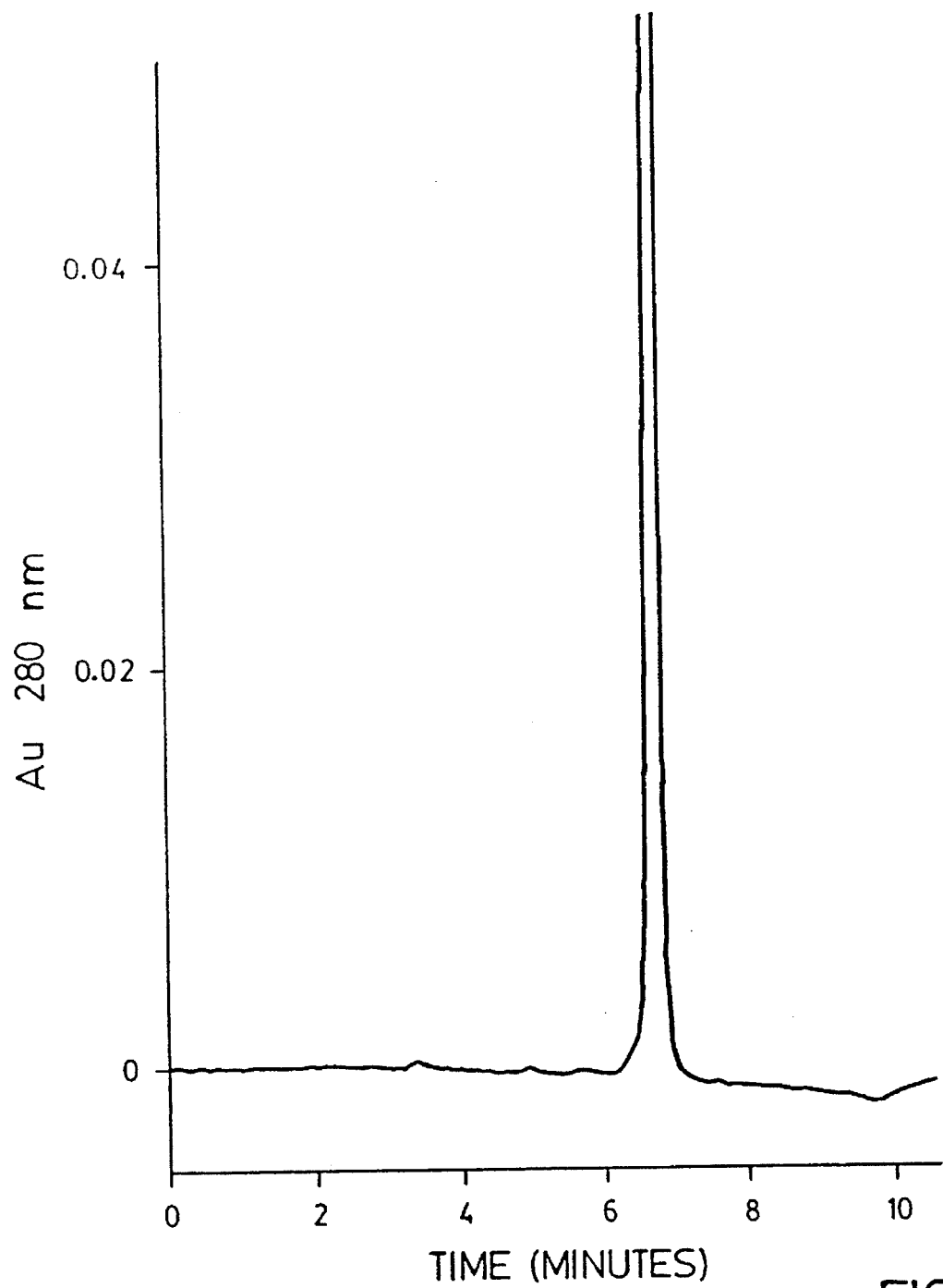
FIG. 4 is an analytical anionic exchange chromatogram derived from the results of Example 4 below.

A 1×10 cm column packed with Perseptive Poros HS-50 was washed with 4 column volumes of 1N NaCl and equilibrated with 5 mM Tris buffer, pH 7.5. After equilibration 120 ml of a 2.0% (2 g/100 ml) anion-exchange purified hemoglobin ~95% HbAo) in 5 mM Tris, pH 7.5, prepared as described in Examples 2 and 3, was loaded onto the column at 0.78 ml/min (1 cm/min). The column was overloaded to an effective capacity of 300 mg of the solute per ml of resin, and the eluant was collected. The column was then washed with 2 column volumes of 5 mM Tris, pH 7.5 buffer and this eluant was pooled with eluant collected during loading. The column was then washed with 1N NaCl to elute the retained proteins, and this was discarded. The hemoglobin eluant from the anion-exchange resin was analyzed on an analytical anion-exchange column using a pH gradient, and was determined to be >99% HbAo, as shown on FIG. 4, with a recovery of about 90% of the HbAo loaded on to the column.

Example 5

The effect of conductivity on the self-displacement chromatography on an anion-exchange resin (first stage) was studied.

Effective displacement chromatography is critically dependent on the ionic strength of buffer and/or sample, as determined by conductivity. The experiment summarized below in Table 1 was performed feeding crude lysate of Example 1 to the Poros HQ-50 anion exchange resin from PerSeptive Biosystems Inc. The eluant from the column was analyzed by analytical anionic exchange chromatography. The fractions obtained during run no. 1 were all free from detectable acidic contaminants, whereas even the first fraction from run 2 was contaminated with acidic contaminants.

Example 6—Yield as a Function of Protein Load

Overloading the column achieves a higher recovery of purified HbAo. The experiments reported below in Table 2 demonstrate a very high overload on a 10 ml column of cationic exchange Poros HS-50 resin, which ensures all of the binding sites are occupied by the contaminants, allowing a higher recovery of purified HbAo. The overload in the first experiment was 13.5 times the manufacturer's recommendation (308 mg protein/mL). That in the second experiment was about 5 times the manufacturer's recommendation. The higher overloading leads to a significant improvement in recovery of HbAo from the column.

TABLE 2

| Load (mg Protein mL) | THb | pH | mS | Column (L × D) | Buffer | Flow Rate cm/min | Freedom From Basic Contaminants |
|---|---|---|---|---|---|---|---|
| 308 | 3.1 | 7.5 | 0.5 | 9.5 × 1 | Tris | 0.6 | 100% 88% Recovery |
| 216 | 2.9 | 7.4 | 0.6 | 9.5 × 1 | Tris | 0.6 | 100% 77% Recovery |

Example 7—Separation of Crosslinked Hemoglobin from Other Hemoglobin Species Highly purified human deoxyhemoglobin was reacted with the tris acyl (methyl phosphate) ester of 1,3,5-benzenetricarboxylic acid (TMMP) according to the procedure of Kluger et.al., described in U.S. Pat. No. 5,250,665, specifically Example 5 thereof, with minor modification as to reaction time and temperature. The reaction produces a solution of various hemoglobin species, some crosslinked, some chemically modified. Two of these species, constituting in total about 55% of the total product, are desirable for use, in admixture with one another or separately, as the basis of a blood substitute, on account of their (substantially identical) physiological properties. They require separation from the other hemoglobin products in the reaction mixture. The desired products are three-point crosslinked $\beta^1_{82}$<$X_{82\,\beta}$ and two-point crosslinked $\beta1$-X-$82\beta$ (hereinafter TM-Hb).

Figure 5:
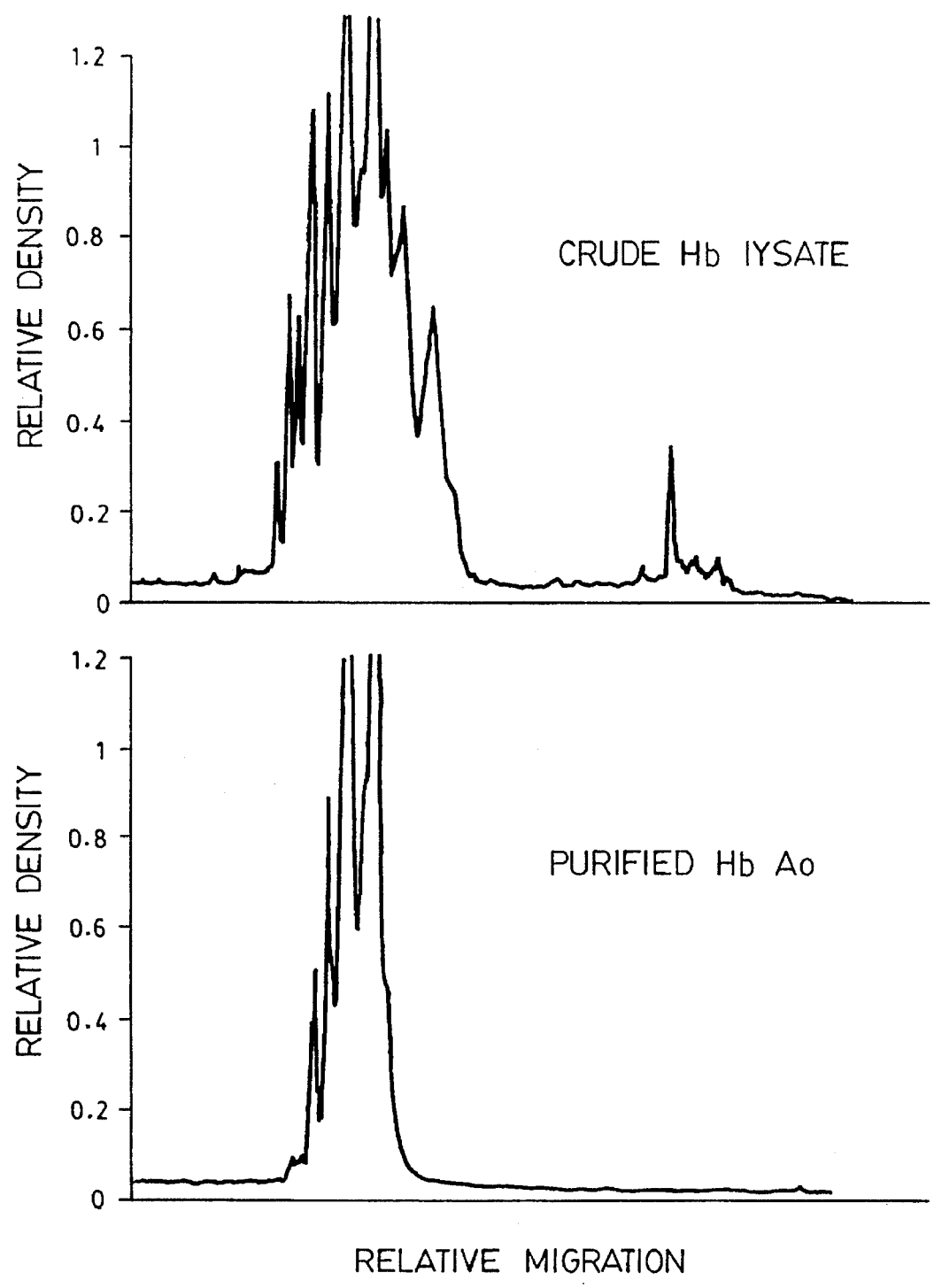
FIG. 5 is a chromatogram illustrating the composition of the starting material used in Example 7 below.

After separation of the unreacted hemoglobin and modified uncrosslinked hemoglobins from the reaction mixture by physico-chemical means, the product solution was subjected to analytical chromatography, and the chromatogram shown in FIG. 5 was obtained. The two desired hemoglobin products, defined as TM-Hb, chromatograph together, as a single peak, and constitute the major peak on FIG. 5. The smaller peaks, at longer elution times, represent other, unwanted hemoglobin species in the reaction product mixture, so similar chemically to the desired species that chemical or physical separation of them therefrom is extremely difficult. However, they all show greater acidity than TM-Hb, based on analysis by anion exchange chromatography.

TABLE 1

| Run | Capacity Load mg/ml | THb | pH | mS | Column (L × D) | Buffer | Flow Rate (cm/min) | Removal of Acidic Contaminants |
|---|---|---|---|---|---|---|---|---|
| 1 | 200 | 3.0 | 8.8 | 0.2/0.4 | 10 × 1 | Tris | 1 | 100% |
| 2 | 200 | 2.8 | 8.8 | 2.85 | 10 × 1 | Tris | 1 | 0% |

Figure 6:
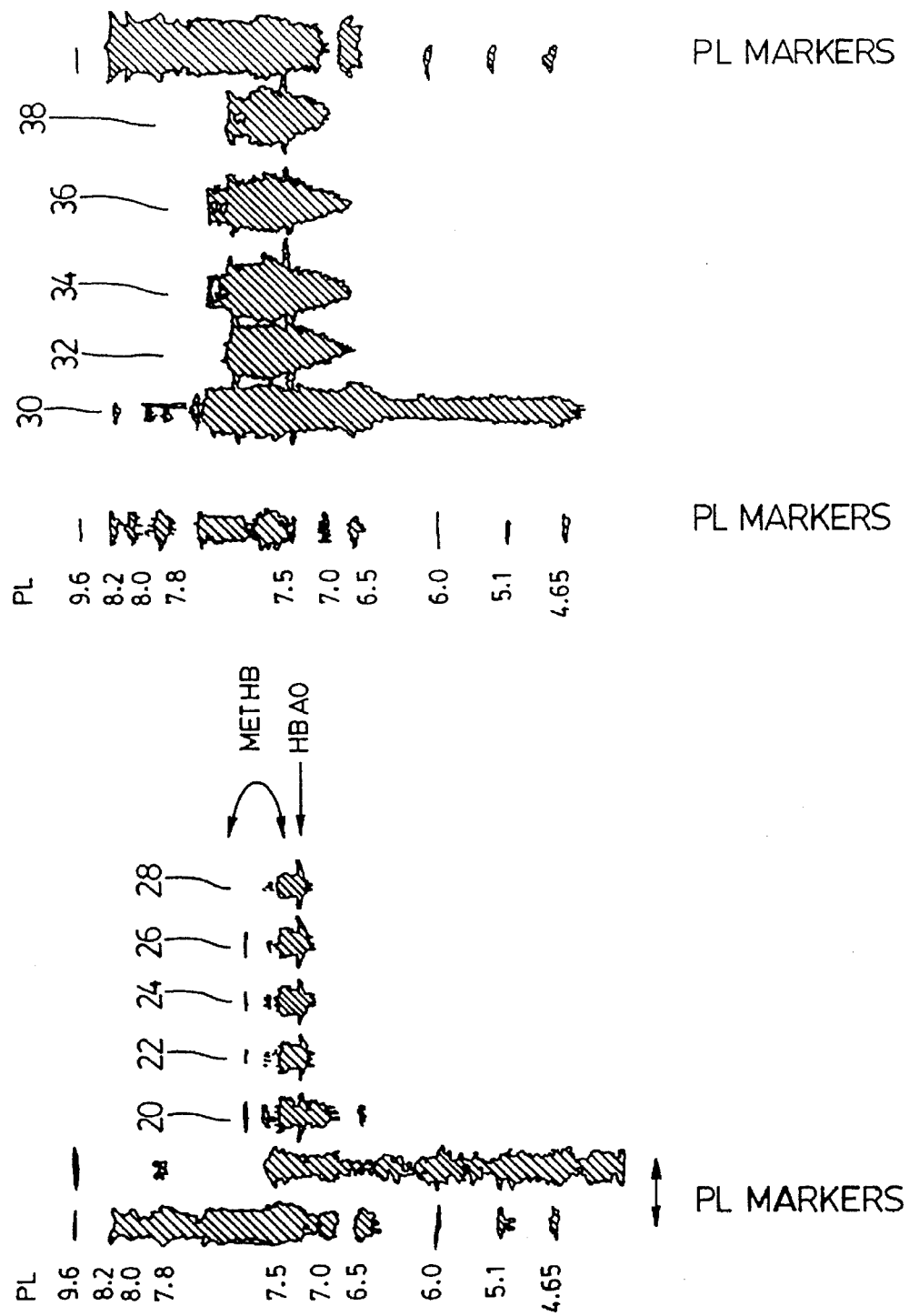
FIG. 6 is a chromatogram illustrating the composition of the product of Example 7 below.

A 9×10.4 cm column packed with the anionic exchange resin, PerSeptive POROS HQ/50, was washed with 4 column volumes of 1N NaCl and equilibrated with 5 mM Tris buffer, pH 9.0. After equilibrating 2.3 L of a 7% (7 g/100 ml) crude TM-Hb solution in 5 mM Tris, prepared as described above, was loaded onto the column at 40 ml/min (0.62 cm/min). The column was overloaded to an effective capacity of 240 mg of the solute per ml of resin and the eluant was collected. The column was then washed with 2 column volumes of 5 mM Tris, pH 9.0 buffer and this eluant was pooled with the eluant collected during loading. The column was then washed with 1N NaCl to sluts the remaining proteins, and this wash eluant was discarded. The purified TM-Hb eluant from the anion exchange resin was analyzed on an analytical anion exchange column using a pH gradient, as described in more detail below, in Example 8. It was determined to be <99% TM-Hb, as shown In FIG. 6, with recovery of 90% of the TM-Hb loaded onto the column. The major peak sown in FIG. 6 is attributable to TM-Hb and a second peak attributable to the methemoglobin form of TM-Hb is observed as a shoulder to the major peak.

Example 8—Analytical Anion Exchange Chromatography

The chromatographic method used to analyze the purity of the hemoglobin products of Examples 2, 3, 4 and 7 above was as follows. The assay was based on a method reported by Huisman and Dozy, *J. Chromatog*, 19, 160–169, (1965). Sample is loaded onto an anion-exchange column at high pH (pH 8.5), such that all the protein binds to the column, and then a pH gradient from pH 8.5 to pH 6.5 is used to sluts the proteins sequentially from the column. Using this chromatographic assay, very similar proteins, e.g. various hemoglobin variants, can be separated.

A 4.6 mm×100 mm analytical anion exchange column from PerSeptive Biosystems was used for the assay. The buffers used were (a) 25 mM Tris+25mM Bis-tris, pH 8.5, and (b) 25 mM Tris+25 mM Bis-tris, pH 6.5. The assay was performed at a flow rate of 5 ml/min. After the column was equilibrated with buffer (b), 10 ul sample (conc. 10 mg THb/ml) was injected on to the column, and the gradient (100% buffer (a) to 100% buffer (b) over 25 column volumes) was started. Eluant was monitored by UV detection at 280 nm to identify protein peaks. FIGS. 3, 4, 5 and 6 are chromatographic profiles of the respective products analyzed by this assay.

We claim:

1. A chromatographic process of separating at least one preselected hemoglobin species from contaminants which have a different acidity from that of said hemoglobin species, which comprises:

selecting a solid chromatographic separation column medium and conditions of use thereof in which both said contaminants and the hemoglobin species have affinity for the column but in which said contaminants have a greater degree of affinity than the hemoglobin species;

feeding a liquid solution comprising a mixture of the hemoglobin species and said contaminants to the column under the selected conditions until the column is substantially fully loaded with hemoglobin species and said contaminants;

further continuing the feed of the liquid solution to cause column overload and subsequent displacement of the hemoglobin species therefrom by said contaminants of greater affinity;

and recovering as eluant from the column a solution of the preselected hemoglobin species substantially free from said contaminants, with the contaminants remaining bound to the column.

2. The process of claim 1 wherein the feed solution has a conductivity less than 3 mS.

3. The process of claim 1 wherein the feed solution is fed to the columnar a rate not greater than 10 cm per minute.

4. The process of claim 1 wherein the column medium and conditions are selected to effect anion exchange chromatography, to retain on the column contaminants of greater acidity than the preselected hemoglobin species.

5. The process of claim 4 wherein the anion exchange process is conducted at pH 5–9 and using a feed solution of low conductivity, less than 3 mS.

6. The process of claim 5 wherein the anion exchange process is conducted at pH 6.5–8.5 and using a feed solution of conductivity less than 1 mS.

7. The process of claim 4 wherein the preselected hemoglobin species is normal adult human hemoglobin HbAo.

8. The process of claim 4 wherein the preselected hemoglobin species is a mixture of three-point crosslinked $\beta^1{}_{82}$>X-$\beta$82 human hemoglobin and two-point crosslinked $\beta$1-X-82$\beta$ human hemoglobin resulting from reaction of hemoglobin with TMMP, and the contaminants are comprised of other hemoglobin species resulting from said reaction.

9. The process of claim 1 wherein the column medium and conditions are chosen to effect cationic exchange chromatography, to retain on the column contaminants more basic than the selected hemoglobin species.

10. The process of claim 9 wherein the cation exchange chromatography is conducted at pH 6.5–8.5 using a feed solution of conductivity less than 3 mS.

11. The process of claim 10 wherein the cation exchange chromatography is conducted at pH 7–7.5 using a feed solution of conductivity less than 1 mS.

12. The process of claim 9 wherein the preselected hemoglobin species is normal adult human hemoglobin HbAo.

* * * * *

UNITED STATES PATENT AND TRADEMARK OFFICE
CERTIFICATE OF CORRECTION

PATENT NO : 5,545,328
DATED : August 13, 1996
INVENTOR(S): Pliura, et al.

It is certified that error appears in the above-identified patent and that said Letters Patent are hereby corrected as shown below:

Column 12, line 21, delete "columnar" and insert --column at--.

Column 12, line 27, delete "5-9" and insert --7-10--.

Column 12, line 30, delete "6.5-8.5" and insert --8.5-9.0--.

Signed and Sealed this

Second Day of December, 1997

BRUCE LEHMAN

*Attest:*

*Attesting Officer*    Commissioner of Patents and Trademarks